US006355621B1

(12) United States Patent
 Fu et al.

(10) Patent No.: US 6,355,621 B1
(45) Date of Patent: Mar. 12, 2002

(54) ANTIGENOMIC OLIGODEOXYNUCLEOTIDES FOR TREATMENT OF INFECTION BY NEGATIVE-STRANDED NONSEGMENTED RNA VIRUSES

(75) Inventors: Zhen Fang Fu, Cherry Hill, NJ (US); Eric Wickstrom, Philadelphia, PA (US); Bernhard Dietzschold, Newtown Square, PA (US); Hilary Koprowski, Wynnewood, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/105,836

(22) Filed: Jun. 26, 1998

Related U.S. Application Data

(60) Provisional application No. 60/051,369, filed on Jun. 27, 1997.

(51) Int. Cl.$^7$ .......................... C07H 21/04; A61K 48/00
(52) U.S. Cl. ............................. 514/44; 435/6; 435/455; 536/23.1; 536/24.1; 536/24.5
(58) Field of Search .................... 435/6, 455; 536/23.1, 536/24.1, 24.5, 24.33, 24.3; 514/44

(56) References Cited

PUBLICATIONS

Agrawal S. "Antisense Oligonucleotides: Towards Clincal Trials" TIBTECH vol. 14:376–387, Oct. 1996.*
Branch A. "A Good Antisense Molecule is Hard to Find" TIBS vol. 23:45–50, Feb. 1998.*
Feldmann et al. "Marburg virus, a Filovirus: Messenger RNAs, Gene Order, and Regulatory Elements of the Replication Cycle" Virus Research vol. 24:1–19, 1992.*
Fu et al., (1996), Oligodeoxynucleotides Complementary to Rabies Virus Genomic RNA Inhibit Rabies Virus Infection.' Abstract W15–9, p. 110, presented at the 15$^{th}$ Annual meeting of the American Society for Virology on Jul. 13–17, 1996.
Agrawal et al., "Site–specific excision from RNA by Rnase H and mixed–phosphate–backbone oligodeoxynucleotides", *Proc Natl Acad Sci USA* 1990, 87, 1401–1405.
Agris et al., "Inhibition of Vesicular Stomatitis Virus Protein Synthesis and Infection by Sequence–Specific Oligodeoxyribonucleoside Methylphosphonates", *Biochemistry* 1986, 25, 6268–6275.
Akhtar et al., "Stability of Antisense DNA Oligodeoxynucleotide Analogs In Cellular Extracts and Sera", *Life Sci* 1991, 49, 1793–1801.
Chomczynski and Sacchi, "Single–Step Method of RNA Isolation by Acid Guanidinium Thiocyanate–Phenol–Chloroform Extraction", *Anal Biochem* 1987, 162, 156–159.
Conzelmann et al., "Molecular cloning and Complete Nucleotide Sequence of the Attenuated Rabies Virus SAD B19", *J Virol* 1990, 175, 484–499.

Dietzschold et al., "Characterization of an antigenic determinant of the glycoprotein that correlates with pathogenicity of rabies virus", *Proc Natl Acad Sci USA* 1983, 80, 70–74.
Dietzschold et al., "Delineation of putative mechanisms involved in antibody–mediated clearance of rabies virus form the central nervous system", *Proc Natl Acad Sci USA* 1992, 89, 7252–7256.
Fu et al., "Differential Effects of Rabies and Borna Disease Viruses on Immediate–Early–and Late–Response Gene Expression in Brain Tissues", *J Virol* 1993, 67, 6674–6681.
Fu et al., "Rabies virus nucleoprotein expressed in and purified form insect cells is efficacious as a vaccine", *Proc Nat'l Acad Sci USA* 1991, 88, 2001–2005.
Gray et al., "Site–specific excision from RNA by Rnase H and mixed–phosphate–backbone oligodeoxynucelotides", *Cancer Res* 1993, 53, 577–580.
Kitajima et al., "Human T–cell Leukemia Virus Virus Type I tax Transformation Is Associated with Increased Uptake of Oligodeoxynucleotides in Vitro and in Vivo", *J Biol Chem* 1992, 267, 25881–25888.
Leiter et al., "Inhibition of influenza virus replication by phosphorothioate oligodeoxynucleotides", *Proc Natl Acad Sci USA* 1990, 87, 3430–3434.
Murphy, F.A., "Rabies Pathogenisis", *Arch Virol* 1977, 54, 279–297.
Offensperger et al., "In vivo inhibition of duck hepatitis B virus replication and gene expression by phosphorothioate modified antisense oligodeoxynucleotides", *EMBO J* 1993, 12, 1257–1262.
Poch et al., Sequence of the 3386 3' nucleotides of the genome of the AVO1 strain rabies virus: structural similarities in the protein regions involved in transcrip *Biochime* 1988, 70, 1019–1029.
Sacramento et al., "Molecular epidemiology of rabies virus in France: comprarison with vaccine strains", *J Gen Virol* 1992, 73, 1149–1158.
Sambrook et al. Molecular Cloning. A Laboratory Manual, 2nd Ed., Cold Spring Harbor Laboratory Press, Cold Spring Harbor, NY, 1989.
Skorski et al., "Suppression of Philadelphia$^1$ leukemia cell growth in mice by BCR–ABL antisense oligodeoxynucleotide", *Proc Natl Acad Sci* 1994, 91, 4504–4508.
Tordo et al., "Walking along the rabies genome: Is the large G–L intergenic region a remmant gene?", *Proc Natl Acad Sci USA* 1986, 83, 3914–3918.

(List continued on next page.)

Primary Examiner—Sean McGarry
(74) Attorney, Agent, or Firm—Thomas Jefferson University

(57) ABSTRACT

Oligodeoxynucleotides complementary to genomic RNA of a negative-stranded nonsegmented RNA virus are provided. Methods of inhibiting infection of cells by a negative-stranded nonsegmented RNA virus and treating animals infected with a negative-stranded nonsegmented RNA virus using these oligodeoxynucleotides are also provided.

33 Claims, No Drawings

PUBLICATIONS

Vickers et al., "Inhibition of HIV–LTR gene expression by oligonucleotides targeted to the TAR element", *Nucleic Acid Res* 1991, 19, 3359–3368.

Wiktor et al., "Antigenic Analysis of rabies and Mokola Virus From Zimbabwe Using Using Monoclonal Antibodies", *Dev Biol Stand* 1984, 57, 199–211.

Wunner et al., "The Molecular Biology of Rabies Viruses", Rev Infect Dis 1988, 10, S771–S784.

Zaia et al., "Inhibition of Human Immunodeficiency Virus by Using an Oligonucleoside Methylphosphonate Targeted to the tat–3 Gene", *J Virol* 1988, 62, 3914–3917.

Zamecnik, P.C. and Stephenson, M.L., "Inhibition of *Rous sarcoma* virus replication and cell transformation by a specific oligodeoxynucleotide", *Proc Nat'l Acad Sci USA* 1978, 75, 280–284.

Zendegui et al., "In vivo stability and kinetics fo absorption and disposition of 3' phosphopropyl amene oligonucleotides"*Nucleic Acid Res* 1992, 20, 307–314.

Fu et al., "Inhibition of rabies virus infection by an oligodeoxynucleotide complementary to rabies virus gnomic RNA", *Antisense and Nucleic Acid Drup Development,* 1996, vol. 6, pp. 87–93.

* cited by examiner

SEQUENCE LISTING (1) GENERAL INFORMATION:

(iii) NUMBER OF SEQUENCES: 18

(2) INFORMATION FOR SEQ ID NO: 1:

(i) SEQUENCE CHARACTERISTICS:
      (A) LENGTH: 16
      (B) TYPE: Nucleic Acid
      (C) STRANDEDNESS: Single
      (D) TOPOLOGY: Linear (iv) ANTI-SENSE: NO (xi) SEQUENCE DESCRIPTION: SEQ ID NO: 1:

ATCAAAGAAA AAACAG                        16

(2) INFORMATION FOR SEQ ID NO: 2:

(i) SEQUENCE CHARACTERISTICS:
      (A) LENGTH: 16
      (B) TYPE: Nucleic Acid
      (C) STRANDEDNESS: Single
      (D) TOPOLOGY: Linear (iv) ANTI-SENSE: YES (xi) SEQUENCE DESCRIPTION: SEQ ID NO: 2:

TTCTCATTTT TGTTGT                        16

(2) INFORMATION FOR SEQ ID NO: 3:

(i) SEQUENCE CHARACTERISTICS:
      (A) LENGTH: 16
      (B) TYPE: Nucleic Acid
      (C) STRANDEDNESS: Single
      (D) TOPOLOGY: Linear (iv) ANTI-SENSE: YES (xi) SEQUENCE DESCRIPTION: SEQ ID NO: 3:

CAGGTTGAGA AGTGTT                        16

```
(2) INFORMATION FOR SEQ ID NO: 4:

(i) SEQUENCE CHARACTERISTICS:
        (A) LENGTH: 16
        (B) TYPE: Nucleic Acid
        (C) STRANDEDNESS: Single
        (D) TOPOLOGY: Linear (iv) ANTI-SENSE: YES (xi) SEQUENCE DESCRIPTION: SEQ ID NO: 4:

TCCAGGATCG AGCATC                                               16

(2) INFORMATION FOR SEQ ID NO: 5:

(i) SEQUENCE CHARACTERISTICS:
        (A) LENGTH: 16
        (B) TYPE: Nucleic Acid
        (C) STRANDEDNESS: Single
        (D) TOPOLOGY: Linear (iv) ANTI-SENSE: NO (xi) SEQUENCE DESCRIPTION: SEQ ID NO: 5:

GATGCTCGAT CCTGGA                                               16

(2) INFORMATION FOR SEQ ID NO: 6:

(i) SEQUENCE CHARACTERISTICS:
        (A) LENGTH: 16
        (B) TYPE: Nucleic Acid
        (C) STRANDEDNESS: Single
        (D) TOPOLOGY: Linear (iv) ANTI-SENSE: YES (xi) SEQUENCE DESCRIPTION: SEQ ID NO: 6:

CGAAAGGAGG GGTGTT                                               16

(2) INFORMATION FOR SEQ ID NO: 7:

(i) SEQUENCE CHARACTERISTICS:
        (A) LENGTH: 16
        (B) TYPE: Nucleic Acid
        (C) STRANDEDNESS: Single
        (D) TOPOLOGY: Linear (iv) ANTI-SENSE: YES (xi) SEQUENCE DESCRIPTION: SEQ ID NO: 7:

CAAAGATCTT GCTGAT                                               16

(2) INFORMATION FOR SEQ ID NO: 8:

(i) SEQUENCE CHARACTERISTICS:
        (A) LENGTH: 16
        (B) TYPE: Nucleic Acid
        (C) STRANDEDNESS: Single
        (D) TOPOLOGY: Linear (iv) ANTI-SENSE: NO (xi) SEQUENCE DESCRIPTION: SEQ ID NO: 8:

ATGAGCAAGA TCTTTG                                               16
```

(2) INFORMATION FOR SEQ ID NO: 9:

(i) SEQUENCE CHARACTERISTICS:
        (A) LENGTH: 73
        (B) TYPE: Nucleic Acid
        (C) STRANDEDNESS: Single
        (D) TOPOLOGY: Linear (iv) ANTI-SENSE: NO (xi) SEQUENCE DESCRIPTION: SEQ ID NO: 9:

```
TGCGAATTGT TGGTCTAGTT TCTTTTTTGT CTGTAACAGT TAACGTTTCG          50

TTTTTACATT GTGGGGATGT TAC                                      73
```

(2) INFORMATION FOR SEQ ID NO: 10:

(i) SEQUENCE CHARACTERISTICS:
        (A) LENGTH: 73
        (B) TYPE: Nucleic Acid
        (C) STRANDEDNESS: Single
        (D) TOPOLOGY: Linear (iv) ANTI-SENSE: NO (xi) SEQUENCE DESCRIPTION: SEQ ID NO: 10:

```
TGCGAATTGT TGGTCTAGTT TCTTTTTTGT CTGTAACAGT TAACGTTTCG          50

TTTTTACATT GTGGGGATGT TAC                                      73
```

(2) INFORMATION FOR SEQ ID NO: 11:

(i) SEQUENCE CHARACTERISTICS:
        (A) LENGTH: 73
        (B) TYPE: Nucleic Acid
        (C) STRANDEDNESS: Single
        (D) TOPOLOGY: Linear (iv) ANTI-SENSE: NO (xi) SEQUENCE DESCRIPTION: SEQ ID NO: 11:

```
TGCGAATTGT TGGTCTAGTT TCTTTTTTGT CTGTCGCAGT TACCGTCTCG          50

TTTTTACATT GTGGAGSTGT TAC                                      73
```

(2) INFORMATION FOR SEQ ID NO: 12:

(i) SEQUENCE CHARACTERISTICS:
        (A) LENGTH: 73
        (B) TYPE: Nucleic Acid
        (C) STRANDEDNESS: Single
        (D) TOPOLOGY: Linear (iv) ANTI-SENSE: NO (xi) SEQUENCE DESCRIPTION: SEQ ID NO: 12:

```
TGCGAATTGT TGTTTTGGTC TCTTCTTTTT CTGTCGCAGT TAACGTTTCG          50

TTTTTACATT GTGGGGATGT TAC                                      73
```

(2) INFORMATION FOR SEQ ID NO: 13:

(i) SEQUENCE CHARACTERISTICS:
        (A) LENGTH: 73
        (B) TYPE: Nucleic Acid
        (C) STRANDEDNESS: Single
        (D) TOPOLOGY: Linear (iv) ANTI-SENSE: NO (xi) SEQUENCE DESCRIPTION: SEQ ID NO: 13:

TGCGAATTGT TGTTTTGGTC TCTTCTTTTT CTGTCGCAGT TAACGTTTCG            50

TTTTTACATT GTGGGGATGT TAC                                        73

(2) INFORMATION FOR SEQ ID NO: 14:

(i) SEQUENCE CHARACTERISTICS:
        (A) LENGTH: 73
        (B) TYPE: Nucleic Acid
        (C) STRANDEDNESS: Single
        (D) TOPOLOGY: Linear (iv) ANTI-SENSE: NO (xi) SEQUENCE DESCRIPTION: SEQ ID NO: 14:

TGCGAATTGT TGTTTTGGTC TCTTCTTTTT CTGTCGCAGT TAACGTTTCG            50

TTTTTACATT GTGGGGATGT TAC                                        73

(2) INFORMATION FOR SEQ ID NO: 15:

(i) SEQUENCE CHARACTERISTICS:
        (A) LENGTH: 73
        (B) TYPE: Nucleic Acid
        (C) STRANDEDNESS: Single
        (D) TOPOLOGY: Linear (iv) ANTI-SENSE: NO (xi) SEQUENCE DESCRIPTION: SEQ ID NO: 15:

TGCGAATTGT TGTTTTGGTC TCTTCTTTTT CTGTCGCAGT TAACGTTTCG            50

TTTTTACATT GTGGGGATGT TAC                                        73

(2) INFORMATION FOR SEQ ID NO: 16:

(i) SEQUENCE CHARACTERISTICS:
        (A) LENGTH: 73
        (B) TYPE: Nucleic Acid
        (C) STRANDEDNESS: Single
        (D) TOPOLOGY: Linear (iv) ANTI-SENSE: NO (xi) SEQUENCE DESCRIPTION: SEQ ID NO: 16:

TGCGAATTGT TGTTTTGGTC TCTACTTCGT CTGTCGCAGT CAACGTTTCG            50

TTTTTACATT GTGGGGATGT TAC                                        73

(2) INFORMATION FOR SEQ ID NO: 17:

(i) SEQUENCE CHARACTERISTICS:
        (A) LENGTH: 73
        (B) TYPE: Nucleic Acid
        (C) STRANDEDNESS: Single
        (D) TOPOLOGY: Linear (iv) ANTI-SENSE: NO (xi) SEQUENCE DESCRIPTION: SEQ ID NO: 17:

TGCGAATTGT TGTTTTAGTC TCTTCTTCGT CTATCACAGT AAACGTTTCG            50

TTTTTACAYY GYGGGGATGT TAC                                        73

(2) INFORMATION FOR SEQ ID NO: 18:

(i) SEQUENCE CHARACTERISTICS:
        (A) LENGTH: 73
        (B) TYPE: Nucleic Acid
        (C) STRANDEDNESS: Single
        (D) TOPOLOGY: Linear (iv) ANTI-SENSE: NO (xi) SEQUENCE DESCRIPTION: SEQ ID NO: 18:

```
TGCGAATTGT TGTTTTAGTC TCTTCTTCAT CTGTCACAGC AAATGTCTCG          50
TTTTTACATT GTGGGGATGT TAC                                      73
```

US 6,355,621 B1

ANTIGENOMIC OLIGODEOXYNUCLEOTIDES FOR TREATMENT OF INFECTION BY NEGATIVE-STRANDED NONSEGMENTED RNA VIRUSES

This application claims the benefit of U.S. Provisional Application No. 60/051,369, filed Jun. 27, 1997.

INTRODUCTION

This invention was made in the course of research supported by Public Health Service grants. The U.S. Government may have certain rights in this invention.

BACKGROUND OF THE INVENTION

Negative-stranded nonsegmented RNA viruses include: paramixoviruses such as Newcastle's disease, mumps and parainfluenza; morbilliviruses such as measles, canine distemper and bovine rinderpest; pneumovirus or respiratory syncytial virus; vesiculovirus; and lyssaviruses such as rabies. The single-stranded negative sense genomic RNA of these viruses act as a direct template for both transcription and replication (Wunner et al. *Rev Infect Dis* 1988, 10, S771–S784). In rabies virus, for example, during the process of transcription a positive strand leader RNA and five monocistronic mRNA are synthesized. These are then translated into individual structural proteins. In the process of replication, the full-length positive strand RNA is synthesized and then becomes the template for the synthesis of progeny negative-stranded nonsegmented genomic RNA.

Vaccination provides a means for preventing infection by several of these more prevalent viruses, i.e., mumps and measles. However, vaccinations are not available for all of these viruses. Further, post-infection treatments are oftentimes unsatisfactory.

For example, it is estimated that more than 50,000 people die of rabies each year. The postexposure treatment recommended by World Health Organization includes administration of rabies vaccine together with antirabies immunoglobulin. The treatment regimen is very effective providing it is initiated within 24–48 hours after exposure. However, such rapid treatment is not always possible. Treatment with rabies vaccines after neuronal infection and dysfunction have occurred may lead to exaggerated immunopathologic disease (Murphy, F. A. *Arch Virol* 1977, 54, 279–297). Once clinical symptoms occur, the disease is usually fatal. There is no treatment or intervention currently available.

Oligodeoxynucleotides (ODN), which are complementary to certain message or viral sequences, have been reported to inhibit specific gene expression or virus infection (Zamecnik, P. C. and Stephenson, M. L. *Proc Nat'l Acad Sci USA* 1978, 75, 280–284). ODN hybridization to complementary RNA sequences inhibits the processing, nuclear transport, or translation of mRNA by blocking the access of functional machinery to requisite mRNA sequences, and the formation of DNA-RNA hybrids leads to RNA cleavage by means of RNase H activities (Agrawal et al. *Proc Natl Acad Sci USA* 1990, 87, 1401–1405). Thus, production of gene products is inhibited, reduced or shut off (Zamecnik, P. C. and Stephenson, M. L. *Proc Nat'l Acad Sci USA* 1978, 75, 280–284). ODN have been used widely to study gene expression (Wickstrom, E. *Prospects for Antisense Nucleic Acid Therapy for Cancer and AIDS*, Wiley-Liss, New York, 1991) and to inhibit tumor growth (Agrawal, S. *Oligonucleotide Therapeutic Approach: Near Clinical Development*, Humana Press, New York, 1996). Antisense ODN to oncogenes, such as c-myb, c-Ha-ras, bcr-abl, or NF-kB, have been reported to inhibit the growth of tumor cells in vitro and in vivo (Kitajima et al. *J Biol Chem* 1992, 267, 25881–25888; Gray et al. Cancer Res 1993, 53, 577–580; Skorski et al. Proc Natl Acad Sci 1994, 91, 4504–4508). One of the first successful demonstrations of using antisense to inhibit virus infection was performed in Rous sarcoma virus in cell culture (Zamecnik, P. C. and Stephenson, M. L. *Proc Nat'l Acad Sci USA* 1978, 75, 280–284). Subsequently, it has been shown that ODN specific to viruses, when added into culture medium, can protect cultured cells to varying extents from infection by a variety of viruses, such as influenza virus (Leiter et al. *Proc Natl Acad Sci USA* 1990, 87, 3430–3434), vesicular stomatitis virus (VSV) (Agris et al. *Biochemistry* 1986, 25, 6268–6275), duck hepatitis virus (Offensperger et al. *EMBO J* 1993, 12, 1257–1262), and human immunodeficiency virus type 1 (HIV-1) (Zaia et al. *J Virol* 1988, 62, 3914–3917). Most of the ODN used to inhibit virus infections are antisense DNA complementary to different viral transcripts. However, ODN to other targets have also been shown to inhibit virus infection, such as the TAR element of HIV-1 (Vickers et al. *Nucleic Acid Res* 1991, 19, 3359–3368). Further, in a brief abstract made available to the public in May of 1996, Fu et al. disclosed that ODNs complementary to rabies virus genomic RNA blocked almost completely rabies virus infection at concentrations as low as 2 µM, while ODNs complementary to vial transcripts did poorly even at concentrations as high as 20 µM (Fu et al., Abstract W15-9, page 110, presented at the 15th Annual Meeting of the American Society for Virology on Jul. 13–17, 1996). This abstract also teaches that the antigenomic ODNS inhibited cell-to-cell spread of the rabies virus and it is suggested that ODNS complementary to rabies virus genomic RNA may have potential to be used for therapy in clinical rabies.

It has now been found that antigenomic ODN targeted to negative strand genomic RNA of nonsegmented RNA viruses are effective inhibitors of viral transcription and may be useful in the treatment and prevention of infection by negative-stranded nonsegmented RNA viruses.

SUMMARY OF THE INVENTION

An object of the present invention is to provide oligodeoxynucleotides complementary to genomic RNA of negative-stranded nonsegmented RNA viruses.

Another object of the present invention is to provide a method of inhibiting infection of cells by a negative-stranded nonsegmented RNA virus which comprises exposing cells to an effective amount of an oligodeoxynucleotide complementary to genomic RNA of a negative-stranded nonsegmented RNA virus so that infection of the cells by the virus is inhibited.

Yet another object of the present invention is to provide a method of treating animals infected with a negative-stranded nonsegmented RNA virus which comprises administering to an animal infected with a negative-stranded nonsegmented RNA virus an effective amount of an oligodeoxynucleotide complementary to genomic RNA of the negative-stranded nonsegmented RNA virus.

DETAILED DESCRIPTION OF THE INVENTION

Oligodeoxynucleotides (ODN) complementary to the genomic RNA of negative-stranded nonsegmented RNA viruses have now been found to block virus infection. Further, the oligodeoxynucleotides of the present invention have been found to be more effective inhibitors of viral transcription and replication than antisense oligodeoxynucleotides targeted to mRNA of the viruses.

The effects of antigenomic ODNs in blocking infection by negative-stranded nonsegmented RNA virus were studied with eight 16 mer ODNs targeted to rabies virus. The sequences and targets of these ODNs are listed in the following Table 1.

TABLE 1

SEQUENCES AND TARGETS OF THE ODNS

| ODN | SEQUENCE | SEQ ID NO | TARGET |
| --- | --- | --- | --- |
| RH+1 | ATCAAAGAAAAAACAG | 1 | nts 16–31 of 3' end of negative strand |
| RE-1 | TTCTCATTTTTGTTGT | 2 | nts 16–31 of 3' end of positive strand |
| RL-1 | CAGGTTGAGAAGTGTT | 3 | upstream noncoding region of rabies virus L mRNA |
| RL-2 | TCCAGGATCGAGCATC | 4 | initiation region of rabies virus L mRNA |
| RL+2 | GATGCTCGATCCTGGA | 5 | sense ODN to RL-2 |
| RNS-1 | CGAAAGGAGGGGTGTT | 6 | upstream noncoding region of rabies virus NS mRNA |
| RNS-2 | CAAAGATCTTGCTGAT | 7 | initiation region of rabies virus NS mRNA |
| RNS+2 | ATGAGCAAGATCTTTG | 8 | sense ODN to RNS-2 |

Inhibitory activities of these ODNs were tested in baby hamster kidney (BHK) and mouse neuroblastoma (NA, clone 1300) cells. BHK and NA cells grown in 24-well plates were infected with rabies virus ERA strain (derived from the same isolate as SAD B19, Sacramento et al. *J Gen Virol* 1992, 73, 1149–1158) at a multiplicity of infection (moi) of approximately 5 focus-forming units (ffu) per cell to ensure that 100% of the cells were infected. After a one hour incubation, the viral inoculum was removed and fresh medium was added with different ODNs to a final concentration of 20 µM. ODNs were further added to culture medium at the same concentration at 3 and 5 hours post infection (p.i.). The cells were cultured for another 16 hours before harvesting. The cell pellets were used for RNA extraction and Northern blot hybridization, using rabies virus N cDNA or G3PDH cDNA as probes, and the supernatants were used for virus titration by the fluorescent focus forming assay.

Northern blot analysis revealed that rabies virus transcription was almost completely inhibited with ODN RH+1 (SEQ ID NO: 1), which is complementary to the 3' end of rabies virus negative-strand genomic RNA. Antigenomic ODN to the positive-strand intermediate genomic RNA (RE-1; SEQ ID NO: 2) and antisense ODNs to different mRNAs showed little or no inhibitory activity at this concentrations. Virus titration revealed no infectious virus in the supernatants of cells (BHK and NA) infected with rabies virus and treated with antigenomic ODN RH+1 (SEQ ID NO: 1), while varying titers of virus were detected in cells treated with other ODNs. Thus, these studies indicate that antigenomic ODNs are most effective at inhibiting negative-stranded nonsegmented RNA viruses such as rabies virus in cell culture. See Table 2.

TABLE 2

RABIES VIRUS TITERS FROM CULTURE SUPERNATANTS TREATED OR UNTREATED WITH ODN

| ODN | BHK Virus Titer (ffu) | NA Virus Titer (ffu) |
| --- | --- | --- |
| None | $10^2$ | $4 \times 10^2$ |
| RH+1 | 0 | 0 |
| RE-1 | $4.5 \times 10^1$ | $4 \times 10^2$ |
| RL-1 | ND | ND |
| RL-2 | $4.5 \times 10^1$ | $9 \times 10^1$ |
| RL+2 | $4.5 \times 10^1$ | $5 \times 10^1$ |
| RNS-1 | ND | ND |
| RNS-2 | $1.5 \times 10^1$ | $5 \times 10^1$ |
| RNS+2 | $4.5 \times 10^1$ | $1.3 \times 10^2$ |

Additional experiments in cell culture indicate that the ability of the ODNs of the present invention to inhibit viral protein synthesis and production results from blocking of viral transcription. In these experiments, viral protein synthesis was measured in RH+1 treated NA cells. NA cells grown on 24 well plates were infected with ERA strain of rabies virus. Cells in one well were treated with ODN RH+1 while cells in a second well were left untreated. Cells were harvested 16 hours after addition of RH+1 and subjected to SDS-PAGE and Western blot analysis using anti-glycoprotein (G) antibody, Rabies virus G protein was detected in the untreated cells infected with rabies virus. However, the G protein was not detected in infected cells treated with RH+1.

Optimal concentrations of ODN resulting in inhibition of rabies virus were determined. RH+1 (SEQ ID NO: 1) was diluted and added to infected NA cells at final concentrations of 10, 5, 2, and 1 µM, respectively. Cells were harvested 24 hours after virus infection for Northern Blot hybridization. Concentrations of RH+1 as low as 2 µM showed strong inhibition of rabies virus transcription and at 1 µM, RH+1 inhibited more than 70% of rabies virus transcription.

Phosphorothioate and methylphosphonate analogs have been reported to have stronger activity in gene inhibition compared to ordinary ODNs with phosphodiester linkage due to their relatively longer half-life and increased resistance to nuclease digestion (Akhtar et al. *Life Sci* 1991, 49, 1793–1801; Agris et al. *Biochemistry* 1986, 25, 6268–6275; Agrawal et al. *Proc Nat'l Acad Sci USA* 1990, 87, 1401–1405). Furthermore, while phosphodiester ODNs failed to inhibit replication of influenza viruses at concentrations up to 80 µM, it was shown that phosphorothioate ODNs inhibited virus replication at concentrations as low as 1.25 µM (Leiter et al. *Proc Natl Acad Sci* 1990, 87, 3430–3434). Accordingly, experiments were performed to determine whether phosphorothioate analogs of the antigenomic ODNs of the present invention are more efficacious. A phosphorothioate analog of antigenomic ODN RH+1 having the sequence 5'-AsTsCsAsAsAsGsAsAsAsAsAsAsCsAsG-3' (SEQ ID NO: 1) referred to herein as RH+1S was synthesized. However, no inhibition of rabies virus at any of the concentrations of RH+1S including 10, 5, 2, and 1 µM was observed.

The ability of the ODNs of the present invention to inhibit spread of these viruses from cell to cell in culture was also demonstrated. It was found that in NA cells treated with antigenomic ODN RH+1 at a concentration of 20 µM, rabies virus remained in the originally infected cells and did not spread to neighboring cells even at 72 hours p.i. In contrast, rabies virus spread quickly in untreated NA cells, and all cells were infected with rabies virus by 72 hours p.i.

In vitro inhibition by ODN RH+1 has also been correlated to in vivo activity. Rats, intranasally infected with rabies virus CVS-24 strain, were used as this model with intranasal infections is used routinely for the study of rabies pathogenesis. All infected animals develop rabies 5 to 6 days following infection. See e.g., Fu et al. *J Virol* 1993, 67, 6674–6681. In these experiments, miniosmotic pumps filled with ODN RH+1, a random ODN, or saline were surgically implanted in the rats for continuous delivery for 7 days of micromolar quantities of the ODN directly to the brain, prior to infection with the rabies virus. All the infected animals were healthy until the 5th day following infection when one of the rats treated with random ODN was paralyzed. By the 6th post infection day all rats treated with random ODN and saline were found paralyzed. However, only three rats treated with RH+1 ODN were paralyzed while 2 of the RH+1 ODN treated rats remained healthy. Levels of viral transcript in brain tissue from these rats were 100 to 1000 times less as compared to the sick rats, thus indicating that rabies virus infection in the CNS of the two healthy rats was inhibited by the antigenomic ODN.

While these experiments were performed with the CVS-24 strain of rabies virus, sequence analysis of the 3' end of rabies virus genomic RNA from multiple strains of rabies virus revealed conserved and variable regions thus indicating that any antigenomic ODNs complementary to at least a portion of the conserved regions would be effective in inhibiting multiple viral strains. The first 58 nucleotides of the 3' end of rabies virus genomic RNA are transcribed into the leader RNA in infected cells (Tordo et al. *Proc Natl Acad Sci USA* 1986, 83, 3914–3918. Comparison of the 3' end sequences of genomic RNA among rabies virus strains sequenced to date revealed only three nucleotide differences between PV and SAD B19 strains (at positions 36, 43 and 47, Tordo et al. 1986; Conzelmann et al. *J Virol* 1990, 175, 484–499), and six nucleotide differences between PV and AV01 strains (at positions 17, 20, 25, 29, 43, and 47; Tordo et al. 1986; Poch et al. Biochime 1988, 70, 1019–1029). The 3' end of the genome of several virus variants was also sequenced and compared with the published sequences for SAD B19, PV and AV01. A comparison of the sequences is shown in Table 3. SAD B19 and ERA are derived from the same original isolate with different passage history and PV is the original Pasteur isolate (Sacramento et al. 1992). AV01 and F3 are derived from CVS-11 (Dietzschold et al. *Proc Natl Acad Sci USA* 1983, 80, 70–74; Poch et al. 1988). All these viruses are laboratory adapted and have gone through numerous passages in laboratory animals and cell cultures. Coyote street rabies virus (COSV) and Thailand dog rabies virus (TLDV) are wildtype viruses isolated from dogs (coyotes) from the United States and Thailand, respectively. Silver haired bat rabies strain (SHBV) is the silver haired bat isolate which has been associated with many of the recent human cases in the United States.

TABLE 3

SEQUENCE DATA FROM 3' END OF RABIES VIRUS GENOMIC RNA

| VIRUS | SEQUENCE FROM 3' END OF GENOMIC RNA | SEQ ID NO: |
|---|---|---|
| ERA | TGCGAATTGTTGGTCTAGTTTCTTTTTTGTCTGTAAC AGTTAACGTTTCGTTTTTACATTGTGGGGATGTTAC | 9 |
| SAD | TGCGAATTGTTGGTCTAGTTTCTTTTTTGTCTGTAAC AGTTAACGTTTCGTTTTTACATTGTGGGGATGTTAC | 10 |

TABLE 3-continued

SEQUENCE DATA FROM 3' END OF RABIES VIRUS GENOMIC RNA

| VIRUS | SEQUENCE FROM 3' END OF GENOMIC RNA | SEQ ID NO: |
|---|---|---|
| PV | TGCGAATTGTTGGTCTAGTTTCTTTTTTGTCTGTCGC AGTTACCGTCTCGTTTTTACATTGTGGAGS TGTTAC | 11 |
| CVS11 | TGCGAATTGTTGTTTTGGTCTCTTCTTTTTCTGTCGC AGTTAACGTTTCGTTTTTACATTGTGGGGATGTTAC | 12 |
| CVS24 | TGCGAATTGTTGTTTTGGTCTCTTCTTTTTCTGTCGC AGTTAACGTTT CGTTTTTACATTGTGGGGATGTTAC | 13 |
| AV01 | TGCGAATTGTTGTTTTGGTCTCTTCTTTTTCTGTCGC AGTTAACGTTTCGTTTTTACATTGTGGGGATGTTAC | 14 |
| F3 | TGCGAATTGTTGTTTTGGTCTCTTCTTTTTCTGTCGC AGTTAACGTTTCGTTTTTACATTGTGGGGATGTTAC | 15 |
| COSV | TGCGAATTGTTGTTTTGGTCTCTACTTCGTCTGTCGC AGTCAACGTTTCGTTTTTACATTGTGGGGATGTTAC | 16 |
| TLDV | TGCGAATTGTTGTTTAGTCTCTTCTTCGTCTATCAC AGTAAACGTTTCGTTTTTACAYYGYGGGGATGTTAC | 17 |
| SHBV | TGCGAATTGTTGTTTTAGTCTCTTCTTCATCTGTCAC AGCAAATGTCTCGTTTTTACATTGTGGGGATGTTAC | 18 |

The first 11 nucleotides of the 3' end of genomic RNA are assumed to be conserved. Sequences from nucleotides 12 to 36 showed some variation; sequences from 37 to 58 (the end of the leader transcript) were more conserved even among the wildtype isolates. Sequences from 59 to 73, which encodes the 5' untranslated regions up to AUG codon of the N transcript are identical among all strains except for PV strains, which showed a one nucleotide differences. As will be obvious to those of skill in the art upon this disclosure, ODNs targeted to other conserved portions of the negative strand of the rabies virus genomic RNA can be designed in accordance with the teachings provided herein. Further, while the exemplified sequences used in the experiments described herein are 16 mer, it is believed that deoxynucleotides of ranging in length from about 10 to about 20 nucleotides would be useful. While absolute complementarity is not required, it is preferred that the deoxynucleotides have no more than one mismatch. Further, it is believed that ODNs targeted to the genomic RNA of other negative-stranded nonsegmented RNA viruses will also be effective as antiviral agents. Examples of other negative stranded nonsegmented RNA viruses include, but are not limited to, paramixoviruses such as Newcastle's disease, mumps and parainfluenza; morbilliviruses such as measles, canine distemper and bovine rinderpest; pneumovirus or respiratory syncytial virus; and vesiculovirus. ODNs targeted to the genomic RNA of these viruses can be designed routinely by those of skill in the art in accordance with the disclosure provided herein.

The ODNs of the present invention are useful in inhibiting infection of cells by a negative-stranded nonsegmented RNA virus. In this method, cells are contacted with an effective amount of an oligodeoxynucleotide complementary to genomic RNA of a negative-stranded nonsegmented RNA virus so that infection of the cells by the virus is inhibited. By "effective amount" it is meant a concentration of ODN which inhibits viral transcription and replication in cells. Such concentrations can be routinely determined in accordance with the methods described herein.

Further, as demonstrated by the in vivo data, ODNs of the present invention which are effective in inhibiting transcription and replication of a negative-strand nonsegmented RNA virus in cell culture are also expected to be useful in treating animals infected with this virus. Appropriate dosing regimes, route of administration and pharmaceutical vehicles can be routinely selected by one of skill in accordance with the virus being treated. For example, for treatment of rabies virus, it is preferred that the oligodeoxynucleotide be administered introcerebroventricularly in a sterile normal saline solution at a concentration of about 5 to about 75 mM.

The following nonlimiting examples are provided to further illustrate the present invention.

EXAMPLES

Example 1
Viruses and cells

Rabies virus Evelyn-Rokitnicki-Abelseth (ERA) strain was grown in confluent baby hamster kidney (BHK) and mouse neuroblastoma (NA, clone 1300) cells in accordance with procedures described by Fu et al. *Proc Nat'l Acad Sci USA* 1991, 88, 2001–2005.

Example 2
Oligodeoxynucleotides (ODN)

Eight 16-mer ODN were designed. See Table 1 for sequences and targets. ODN synthesis was performed with β-cyanoethyl phosphoamidites on a 394 DNA-RNA synthesizer (Applied Biosystems, Foster City, Calif). ODN were purified by reverse-phase chromatography.

Example 3
Treatment of cell culture with ODN

BHK or NA cells were infected with rabies virus ERA strain at multiplicity of infection (MOI) Of 5 focus-forming units (ffu) per cell. After 1 hour of incubation, virus inoculum was removed, and fresh medium was added with each ODN at a final concentration of 20 $\mu$M. ODN were further added to culture medium at the same concentration at 3 to 5 hours post infection (p.i.). The cells were cultured for another 16 hours and then harvested. The cell pellets were used for RNA extraction, and the supernatants were used for virus titration.

Example 4
RNA Extraction and Northern Blot Hybridization

Total RNA was extracted from cells in accordance with procedures described by Chomczynski and Sacchi *Anal Biochem* 1987, 162, 156–159. The extracted RNA was then used for Northern blot hybridization using rabies virus nucleoprotein (N) gene probe as described by Dietzschold et al. *Proc Natl Acad Sci USA* 1992, 89, 7252–7256. This probe measures rabies virus transcription. Total RNA was denatured with 10 mM sodium phosphate buffer, pH 7.4/50% (v/v) formamide (Sigma Chemical Co., St. Louis, Mo.) at 65° C. for 15 minutes and electrophoresed in a 1.2% agarose gel, containing 1.1 M formaldehyde and 10 mM sodium phosphate buffer (pH 7.4). RNA was transferred and covalently fixed onto nylon membrane. Two probes were used for the hybridization, rabies virus nucleoprotein cDNA described previously by Fu et al. *Proc Natl Acad Sci USA* 1991, 88, 2001–2005, and housekeeping gene glyceraldehyde-3-phosphate dehydrogenase (G3PDH) cDNA described previously by Fu et al. *J Virol* 1993, 67, 6674–6681. The probes were labeled with [$^{32}$P]dCTP by using a nick translation kit (Boehringer Mannheim, Indianapolis, Ind.).

Example 5
Virus titration

Virus titration was performed in accordance with procedures described by Wiktor et al. *Dev Biol Stand* 1984, 57, 199–211. The supernatants collected from individual cultures were serially diluted (three-fold) and mixed with freshly prepared BHK cells in a 96-well plate. Twenty-four hours after infection, the cells were fixed in 80% acetone and stained with FITC-conjugated antirabies virus antibody. Virus titers were calculated from the numbers of fluorescent foci detected in cells infected with the highest virus dilution and expressed as focus-forming units.

Example 6
Virus spread inhibition assay

Virus spread inhibition assay was performed in accordance with procedures described by Dietzschold et al. *Proc Natl Acad Sci USA* 1992, 89, 7252–7256. Confluent NA calls grown in 24-well plates were infected with rabies virus ERA strain at 0.1 ffu per cell. After 1 hour absorption, the viral inoculum was removed, and fresh culture medium containing ODN RH+1 at a final concentration of 20 $\mu$M was added. RH+1 at the same concentration was added again to the culture medium at 24 and 48 hours p.i. NA cells infected with rabies virus at the same MOI, but without addition of ODN, were included as controls. The cells were fixed in 80% acetone and stained with FITC-conjugated antirabies virus antibody at 24, 48 and 72 hours p.i.

Example 7
In vivo inhibition of rabies virus

Rats intranasally infected with rabies virus CVS-24 strain were used. This animal model is used routinely for the study of rabies pathogenesis and all infected animals develop rabies 5 to 6 days following infection. See e. g., Fu et al. *J Virol* 1993, 67, 6674–6681.

Two ODNs were synthesized for this study, ODN RH+1, complementary to nucleotides 16 to 31 at the 3' end genomic RNA of rabies virus CVS-24 strain and a random ODN with ACTG repeat. To protect the ODNs from 3'-exonuclease activities in the brain, the 3' ends were modified with phosphopropyl amine in accordance with procedures described by Zendegui et al. *Nucleic Acid Res* 1992, 20, 307–314. ODNs were diluted in saline to a concentration of 15 mM. The final concentration in the CSF is expected to be approximately 1.5 $\mu$M.

Miniosmotic pump model Alzet 2001 (ALZA Corp., Palo Alto, Calif.) which can deliver ODN continuously into the CNS at 1 $\mu$l/hour for 7 days (allowing for maintenance of micromolar concentrations of ODN in these animals for the entire treatment period) was surgically implanted into each rat prior to infection, in accordance with manufacturer's instructions. Indwelling 22-gauge stainless steel cannulae were implanted stereotactically in the lateral ventricle. Miniosmotic pumps with a 5 cm length polyethylene tubing were implanted subcutaneously, fitted to the stainless steel cannula and fixed in place with dental cement. Groups of rats (5/group) were implanted with pumps filled with ODN RH+1, ODN random or saline, respectively. Five of the five rats given ODN RH+1, two of the five rats given the random ODN, and three of the five rats with only saline survived the surgery. One day following the surgical implantation of the pumps, rats were infected intranasally with 30 $\mu$l of a 10% mouse brain suspension containing 2.4×10$^5$ MICLD$_{50}$ (50% mouse intracerebral lethal dose) of rabies CVS-24 strain.

All animals were observed daily for clinical signs of rabies. Since the pumps were designed to deliver ODN for only 7 days, experiments were terminated at this day and all animals were sacrificed. Brains from these rats were removed and stored at −80° C. for analysis of rabies virus RNA.

Example 8
Analysis of rabies virus RNA

Total RNA was isolated from frozen rat brains using the Ultraspec RNA method in accordance with the manufacturer's protocol (Biotecx Lab., Inc. Houston, Tex.). Rabies virus N transcript and the transcript of G3PDH were measured by RNase protection assay in accordance with procedures described by Sambrook et al. *Molecular Cloning. A Laboratory Manual*, 2nd Ed., Cold Spring Harbor Laboratory Press, Cold Spring Harbor, N.Y., 1989. A 400 basepair fragment of rabies virus N protein cDNA and a 600 bp fragments of G3PDH cDNA were respectively cloned into pGem-3Z. The negative sense probes were transcribed with T7 polymerase using $^{32}$P-UTP and hybridized to 15 µg total RNA from each of the brains. After a short film exposure (2 hours), similar levels of G3PDH transcripts were detected in all animals paralyzed. After a long exposure (3 days), rabies virus specific RNA was detected in the brains of the two infected rats that showed no clinical signs of rabies. Levels of viral transcript in the rats were 100 to 1000 time less compared to the sick rats, thus indicating that rabies virus infection in the CNS of the two healthy rats was inhibited by the antigenomic ODN.

Example 9
Sequence analysis of 3' end of various strains of rabies virus genomic RNA A primer complementary to the first 11 nucleotides of the 3' end of rabies virus genome which appear to be conserved between strains (5'-ACGCTTAACAA-3'; SEQ ID NO: 19) was used as the reverse primer (primer 3'A). Total RNA extracted from NA cells infected with different rabies virus strains was used for reverse transcription. PCR amplification was performed using primer 3'A and primer 5'A (5'-CACTCAAGCCTAGTGAACGGA-3'; SEQ ID NO: 20) which corresponds to nucleotides 935 to 955 of the sequences encoding rabies virus N protein. PCR products were directly sequenced, using the sequencing primer SA (5'-TTTCCTAGGGTTATACAG-3'; SEQ ID NO: 21) which corresponds to nucleotides 187–204 of the sequences encoding rabies virus N protein.

---

What is claimed is:

1. An oligodeoxynucleotide comprising about 10 to 20 nucleotides complementary to a conserved portion of the genomic RNA of a negative-stranded nonsegmented RNA virus wherein said oligodeoxynucleotide inhibits transcription or replication of the negative-stranded nonsegmented RNA virus.

2. The oligodeoxynucleotide of claim 1 wherein the negative-stranded nonsegmented RNA virus is a rabies virus.

3. The oligodeoxynucleotide of claim 2 comprising SEQ ID NO: 1.

4. A method of inhibiting infection of cells by a negative-stranded nonsegmented RNA virus comprising exposing cells to an effective amount of an oligodeoxynucleotide of claim 1 so that infection of the cells by the virus is inhibited.

5. The method claim 4 wherein the negative-stranded nonsegmented RNA virus is a rabies virus.

6. The method of claim 5 wherein the oligodeoxynucleotide comprises SEQ ID NO: 1.

7. A method of treating animals infected with a negative-stranded nonsegmented RNA virus comprising administering to an animal infected with a negative-stranded nonsegmented RNA virus an effective amount of an oligodeoxynucleotide of claim 1.

8. The method of claim 7 wherein the negative-stranded nonsegmented RNA virus is a rabies virus.

9. The method of claim 8 wherein the oligodeoxynucleotide comprises SEQ ID NO: 1.

10. The oligodeoxynucletie of claim 1 wherein the negative-stranded nonsegmented RNA virus is selected from the group consisting of rabies viruses, paramyxoviruses, morbilliviruses, respiratory syncytial virus and vesiculovirus.

11. The oligodeoxynucleotide of claim 1 wherein the negative-stranded nonsegmented RNA virus is a rabies virus or a paramyxovirus.

12. The method of claim 4 wherein the negative-stranded not segmented RNA virus is selected from the group consisting of rabies viruses, paramyxoviruses, morbilliviruses, respiratory syncytial virus and vesiculovirus.

13. The method of claim 4 wherein the negative-stranded nonsegmented RNA virus is a rabies virus or a paramyxovirus.

14. The the method of claim 7 wherein the negative-stranded nonsegmented RNA virus selected from the group consisting of rabies viruses, paramyxoviruses, morbilliviruses, respiratory syncytial virus and vesiculovirus.

15. The the method of claim 7 wherein the negative-stranded nonsegmented RNA virus is a rabies virus or a paramyxovirus.

16. The oligodeoxynucleotide of claim 1 wherein said oligodeoxynucleotide is protected from 3'-exonuclease activity.

17. The oligodeoxynucleotide of claim 16 wherein said protection from 3'-exonuclease activity comprises modification of the 3' end of said oligodeoxynucleotide with phosphopropyl amine group.

18. The oligodeoxynucleotide of claim 17 wherein the negative-stranded nonsegmented RNA virus is selected from the group consisting of rabies viruses, paramyxoviruses, morbilliviruses, respiratory syncytial virus and vesiculovirus.

19. The oligodeoxynucleotide of claim 17 wherein the negative-stranded nonsegmented RNA virus is a rabies virus or a paramyxovirus.

20. The oligodeoxynucleotide of claim 17 wherein the negative-stranded nonsegmented RNA is a rabies virus.

21. The oligodcoxynuclotide of claim 20 comprising SEQ ID NO: 1.

22. The method of claim 4 wherein said oligodeoxynucleotide is protected from 3'-exonuclease activity.

23. The method of claim 22 wherein said protection from 3'-exonuclease activity comprises modification of the 3' end of said oligodeoxynucleotide with phosphopropyl amine group.

24. The method of claim 23 wherein the negative-stranded nonsegmented RNA virus is selected from the group consisting of rabies viruses, paramyxoviruses, morbilliviruses, respiratory syncytial virus and vesiculovirus.

25. The method of claim 23 wherein the negative-stranded nonsegmented RNA virus is a rabies virus or a paramyxovirus.

26. The method of claim 23 wherein the negative-stranded nonsegmented RNA virus is a rabies virus.

27. The method of claim 26 wherein the oligodeoxynucleotide comprises SEQ ID NO: 1.

28. The method of claim 7 wherein said oligodeoxynucleotide is protected from 3'-exonuclease activity.

29. The method of claim 28 wherein said protection from 3'-exonuclease activity comprises modification 3' end of said oligodeoxynucleotide with phosphopropyl amine group.

30. The method of claim 29 wherein the negative-straded nonsegmented RNA virus is selected from the group consisting of rabies viruses, paramyxoviruses, morbilliviruses, respiratory syncytial virus and vesiculovirus.

31. The method of claim 29 wherein the negative-straded nonsegmented RNA virus is a rabies virus or a paramyxovirus.

32. The method of claim 29 wherein the negative-stranded nonsegmented RNA virus is a rabies virus.

33. The method of claim 32 wherein the oligodeoxynucleotide comprises SEQ ID NO: 1.

\* \* \* \* \*